United States Patent [19]

Felix

[11] 4,228,185
[45] Oct. 14, 1980

[54] N-4-(2',2'-DICHLOROCYCLOPROPROPYL)-PHENYL 2''-IODOBENZAMIDE

[75] Inventor: Raymond A. Felix, Richmond, Calif.

[73] Assignee: Stauffer Chemical Company, Westport, Conn.

[21] Appl. No.: 26,468

[22] Filed: Apr. 2, 1979

[51] Int. Cl.² .................. A01N 9/20; C07C 103/22
[52] U.S. Cl. .................. 424/324; 260/558 D
[58] Field of Search .................. 260/558 D; 426/326

[56] References Cited

U.S. PATENT DOCUMENTS

| | | | |
|---|---|---|---|
| 3,576,869 | 4/1971 | Schellenbaum | 424/324 X |
| 3,969,510 | 7/1976 | Osieka et al. | 424/324 |
| 4,069,335 | 1/1978 | Kawada et al. | 424/324 X |

*Primary Examiner*—Frederick E. Waddell
*Attorney, Agent, or Firm*—Joel G. Ackerman

[57] ABSTRACT

This invention relates to the novel compound N-4-(2',2'-dichlorocyclopropyl)phenyl 2''-iodobenzamide, having the formula

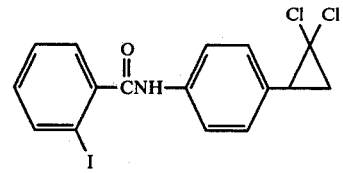

which has been found useful as a fungicide.

3 Claims, No Drawings

N-4-(2',2'-DICHLOROCYCLOPROPROPYL)PHENYL 2''-IODOBENZAMIDE

This invention relates to the novel compound N-4-(2',2'-dichlorocyclopropyl)phenyl 2''-iodobenzamide, having the formula

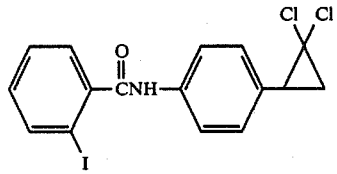

which, as will be seen from the data included herein, possesses certain fungicidal activity.

The compound was prepared by the reaction of 4-(2',2'-dichlorocyclopropyl)aniline with 2-iodobenzoyl chloride. The benzoyl chloride (5.3 grams, 0.02 mole) was dissolved in toluene and cooled with an ice bath. There was then added 4.0 grams (0.02 mole) of the dichlorocyclopropyl aniline and 3 milliliters (0.022 mole) triethylamine. The mixture was stirred for 6 hours, 100 milliliters of ether was added, then washed successively with water, 1 molar hydrochloric acid and 1 molar aqueous sodium hydroxide solution. There was obtained 8 grams (93% of theoretical yield) of a tan solid, melting point 110°–115° C.

FUNGICIDAL EVALUATION

This compound was tested for fungicidal activity by the following procedures.

In vitro vial tests: Tubes containing 5 milliliters of a malt extract broth were prepared. Aliquots of the test compound, dissolved in acetone, were injected through the stopper into the broth, to provide concentrations ranging from 50 ppm downward. The test organisms consisted of two fungi, *Aspergillus niger* (A.n.) van Tieghem and *Penicillium italicum* (P.i.) Wehmer. Three drops of a suspension of each of the fungi were injected into the tubes of malt broth. One week later, the growth of each organism was observed and effectiveness of the chemical was recorded as the lowest concentration in ppm which provided 100% inhibition of growth as compared to untreated inoculated tubes. The results of these tests are found in Table I.

Foliar Preventative Sprays

Bean rust—The chemical was dissolved in an appropriate solvent and diluted with water containing several drops of a wetting agent. Test concentrations, ranging from 1000 ppm downward, were sprayed to run-off on the primary leaves of pinto beans (*Phaseolus vulgaris* L.). After the leaves were dried, they were inoculated with a water suspension of spores of the bean rust fungus (*Uromyces phaseoli* arthur) and the plants were placed in an environment of 100% humidity for 24 hours. The plants were then removed from the humidity chamber and held until disease pustules appeared on the leaves. Effectiveness was recorded as the lowest concentration, in ppm, which provided 75% or greater reduction in pustule formation as compared to untreated, inoculated plants.

Bean powdery mildew—The test chemical was prepared and applied in the same manner as for the bean rust test. After the plants were dry, the leaves were dusted with spores of the powdery mildew fungus (*Erysiphe polygoni* De Candolle) and the plants were retained in the greenhouse until the fungal growth appeared on the leaf surface. Effectiveness was recorded as the lowest concentration, in ppm, which provided 75% or greater reduction in mycelial growth on the leaf surface as compared to untreated, inoculated plants.

Tomato early blight—The test chemical was prepared and applied in the same manner as the bean rust and powdery mildew tests except that 4-week old tomato (*Lycopersicon esculentum*) plants were utilized as the host plant. When the leaves were dry, they were inoculated with a water suspension of spores of the early blight fungus (*Alternaria solani* Ellis and Martin) and placed in an environment of 100% humidity for 48 hours. The plants were then removed from the humidity chamber and held until disease lesions appeared on the leaves. Effectiveness was recorded as the lowest concentration, in ppm, which provided 75% or greater reduction in the number of lesions formed as compared to untreated, inoculated plants.

Bluegrass leaf spot—The test chemical was dissolved in an appropriate solvent and further diluted with a 50:50 acetone:water solution. "Marion" Kentucky bluegrass plants (*Poa pratensis* L.), approximately four weeks old, were sprayed to the point of run-off with the test solutions. Test concentrations ranged from 1000 ppm downwards. After the leaves dried, they were inoculated with a water suspension of *Helminthosperium sativum* Tammel and held at 100% relative humidity for 48 hours. The plants were then held in a greenhouse at 27° C. until diseased lesions appeared on the leaves. Effectiveness was recorded as the lowest concentration in ppm which provided 75% or greater reduction in the number of lesions as compared to untreated inoculated plants.

Foliar Eradicative Sprays

Bean rust—Untreated bean plants were inoculated with spores of the bean rust fungus and placed in an environment of 100% humidity for 24 hours. They were then removed from the humidity chamber and held in the greenhouse for two days to allow the disease to become established. The test chemical was then prepared and applied in the same manner as in the preventative spray tests. Eradicative effectiveness was recorded as the lowest concentration, in ppm, which provided 75% or greater reduction in pustule formation as compared to untreated inoculated plants.

Bean powdery mildew—Untreated pinto bean plants were dusted with spores of the powdery mildew fungus and maintained in the greenhouse until mycelial growth appeared on the leaf surface. The test chemical was then prepared and applied in the same manner as for the preventative spray test. Four days later, the leaves were examined for inhibition of further mycelial growth. Eradicative effectiveness was recorded as the lowest concentration, in ppm, which provided 75% or greater reduction in mycelial growth on the leaf surface as compared to untreated inoculated plants.

Tube Systemic Tests

Bean rust—The chemical was dissolved in an appropriate solvent and diluted with tap water to a series of descending concentrations beginning at 50 ppm. Sixty milliliters of each concentration was placed in a test tube. A pinto bean plant was placed in each tube and supported with a piece of cotton so that only the roots and lower stem were in contact with the test solution. Forty-eight hours later the bean leaves were inoculated with a water suspension of spores of the bean rust fungus and placed in an environment with 100% humidity for 24 hours. The plants were then removed from the humidity chamber and maintained in the greenhouse until the disease pustules appeared on the leaves. Effectiveness was recorded as the lowest concentration, in ppm, which provided 75% or greater reduction in pustule formation as compared to untreated, inoculated plants.

Bean powdery mildew—The test chemical was prepared and applied in the same manner as for the bean rust systemic test. After two days, the leaves were dusted with spores of the powdery mildew fungus and maintained in the greenhouse until mycelial growth appeared on the leaf surfaces. Effectiveness was recorded as the lowest concentration, in ppm, which provided 75% or greater reduction in mycelial growth on the leaf surface as compared to untreated, inoculated plants.

Results of all the above tests are contained in Table 1.

TABLE I

| | Prevent. (ppm) | | | Eradic. (ppm) | | Syst. (ppm) | | In Vitro ppm | |
|---|---|---|---|---|---|---|---|---|---|
| Rust | Mildew | Tom. Blight | Leaf Spot | Rust | Mildew | Rust | Mildew | A.n. | P.i. |
| 500 | 100 | >1000 | 100 | — | 1000 | >50 | >50 | >50 | >50 |

In practice, the pure compound could be used as a fungicide; however, in general, this compound would first be formulated with one or more inert carriers or diluents suitable for fungicidal use before being applied.

Compositions or formulations including this compound may take and be used in any number of solid or liquid forms. Examples of solid forms are dusts, granules, tablets and the like. Some liquid forms are emulsions, solutions, suspensions, emulsifiable concentrates and pastes. Such compositions may contain, in addition to the active compound, various carriers or diluents, surface active agents such as wetting agents and/or emulsifing agents, solvents, adhesives, thickeners, binders, anti-foaming agents and other substances. Solid and liquid formulations including this compound are prepared in the conventional fashion.

The various types of compositions which can be utilized will contain various amounts of the compound according to the type of composition and intended use.

In general, the compositions may contain from 5 to 95% of the active compound, and more preferably from 10 to 85%. Some typical compositions will contain an active compound as follows: wettable powders—25 to 80%, active compound; oil suspensions, emulsions, solutions and emulsifiable concentrates—20 to 85% active compound; dusts and powders—20 to 50% active compound; granules and pellets—5 to 20% compound.

The rate of application of the active compound to a locus at which fungi are to be controlled will depend on the nature of the fungi and plants in connection with which control is desired, and will generally vary from about 0.025 to about 100 pounds per acre (about 0.28 to about 112 kg./ha.)

In addition to the active compound and the various agents utilized for preparing compositions and formulations mentioned above, compositions containing the compound may also contain one or more other active pesticidal agents such as other fungicides, herbicides, insecticides, acaricides, nematocides, bactericides and plant growth regulators. Such compositions may also contain soil disinfectants or fumigants and may further contain fertilizers, thus making it possible to provide multi-purpose compositions containing this compound as well as optionally other pesticides and also fertilizers, all intended and formulated for use at the same locus.

Compositions containing this active compound, in a fungicidally effective amount, may be applied to the locus to be controlled in any conventional manner. Thus, powders and liquid compositions containing the active compound can be applied by the use of power dusters, boom and hand sprayers and spray dusters, or applied from airplanes as dusts and sprays; when applied in the latter method, it may be effective in very low dosages. They need not be admixed with the soil particles, but can be applied merely by sprinkling on the surface of the soil. They may also be applied by addition to irrigation waters supplied to a field or land to be treated. This method of application permits penetration of the compound into the soil as the water is absorbed therein.

What is claimed is:

1. A compound having the formula

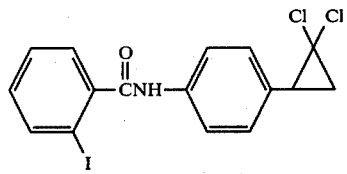

2. A method of controlling fungi comprising applying to the fungi or the locus thereof a fungicidally effective amount of a compound having the formula

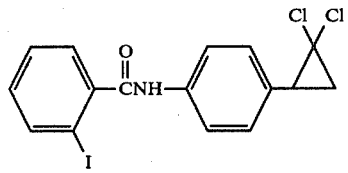

3. A fungicidal composition comprising:
(a) a fungicidally effective amount of a compound having the formula

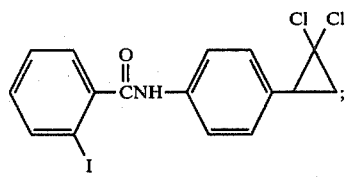

and
(b) a fungicidally suitable inert carrier or diluent.

* * * * *